US00PP10459P

United States Patent [19]

Toyama

[11] Patent Number: Plant 10,459

[45] Date of Patent: Jun. 23, 1998

[54] SWEET CHERRY TREE — 'PC 7222-1'

[75] Inventor: Thomas K. Toyama, Eugene, Oreg.

[73] Assignee: Washington State University Research Foundation, Pullman, Wash.

[21] Appl. No.: 782,654

[22] Filed: Jan. 14, 1997

[51] Int. Cl.[6] ..... A01H 5/00

[52] U.S. Cl. ..... Plt./37

[58] Field of Search ..... Plt./37

*Primary Examiner*—James R. Feyrer

*Attorney, Agent, or Firm*—Chernoff, Vilhauer, McClung & Stenzel

[57] ABSTRACT

A new and distinct variety of self-fertile sweet cherry, *Prunus avium*, tree which bears medium to large 9.1–9.5 grams in weight firm mahogany-red colored fruits. Its exceptional, high quality, attractive fruits ripen four to five days ahead of the commercially grown Bing variety, which it is compared to herein.

3 Drawing Sheets

BACKGROUND AND SUMMARY OF THE INVENTION

The present invention relates to a new variety of sweet cherry tree which bears medium to large, firm, attractive fruits of excellent quality and flavor.

This new variety was developed at the Washington State University's Irrigated Agriculture Research and Extension Center (I.A.R.E.C.) at Prosser, Washington. It was selected from among fourteen (14) seedlings of the variety Stella (unpatented variety)×unknown and was tested as PC 7222-1. Second generation test trees were planted on the Roza Unit of the Center in the spring of 1979 and came into production in 1983.

The new sweet cherry variety ripens 5–6 days before Bing (popular unpatented commercial variety). It is self-fertile, blooms 2–3 days before Bing and is pollen compatible with Bing.

The new cherry variety resembles Bing in shape and appearance. The trees have been consistently productive, bearing fruits comparable in size and as firm as Bing. The fruits are Bing-shaped, glossy and attractive when mature and possess good cracking tolerance.

Fruit stems are medium length, similar to those of Bing. Fruit shape is broadly cordate and the flesh, which colors slowly, is light to medium red.

Fruit buds of PC 7222-1 have greater winter hardiness than Bing as demonstrated by winter freezes at the test site near Prosser in December 1990 and February 1996.

The tree is vigorous and spreading in shape and has proven to be a very precocious and fruitful bearer of early to mid-season high quality cherries.

Soluble solids are equal to or slightly more than Bing when comparing fruits of equal maturity and fruit kept in cold storage at 33°–34° F. for four weeks stored equal to Bing fruits.

The seeds are semi-freestone and small. All second and third generation test trees observed closely have shown no tendency toward the "Cherry Crinkle-leaf" genetic disorder which is common in Bing, as well as in several other varieties of sweet cherry.

Interest in this new variety is for a firm, high quality shipping variety for the early season market. The present new variety fills the gap between the early maturing Chelan variety (U.S. Plant Pat. No. 8545) and the popular commercially grown Bing variety. The present variety fits into this gap period very well, maturing about five days after Chelan and about 5–6 days ahead of Bing.

Trees of the subject variety are vigorous and, following several years of testing, have proven compatible with all common rootstocks used under sweet cherry trees.

Asexual reproduction of this new and distinct variety shows that its desirable characteristics come true to form and are established and transmitted through succeeding propagations by grafting at the test facilities near Prosser.

BRIEF DESCRIPTION OF THE SEVERAL VIEWS OF THE DRAWINGS

In the accompanying photographs, vegetative growth, fruit and seeds are shown in color as nearly true as is reasonably possible to make in color photographs of this nature.

DETAILED DESCRIPTION OF THE INVENTION

Figure 1:
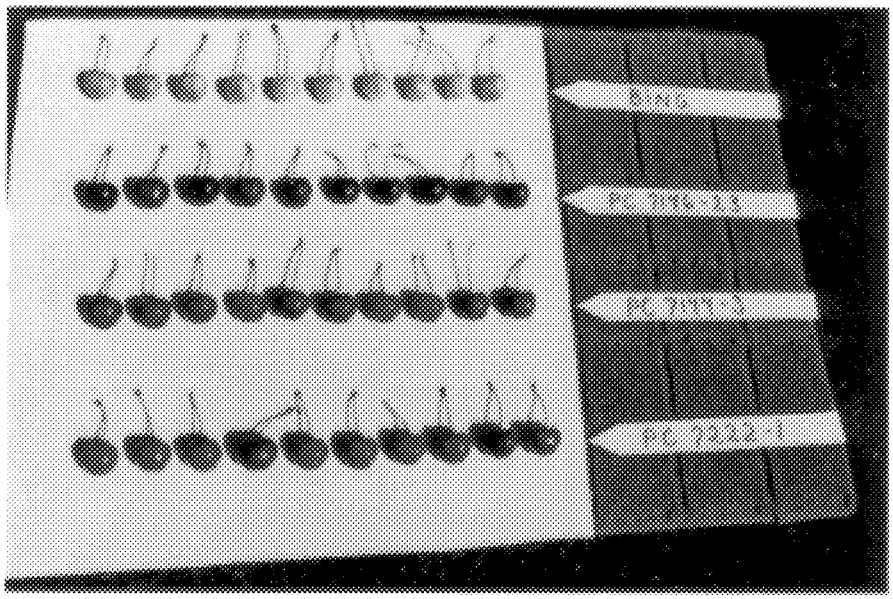
FIG. 1 shows and compares the maturity of fruit picked from trees of the subject variety, PC 7144-3 (unnamed), PC 7146-23 (Chelan) and Bing. The trees were planted in adjacent rows in a test orchard near Wapato, Wash.
Figure 2:
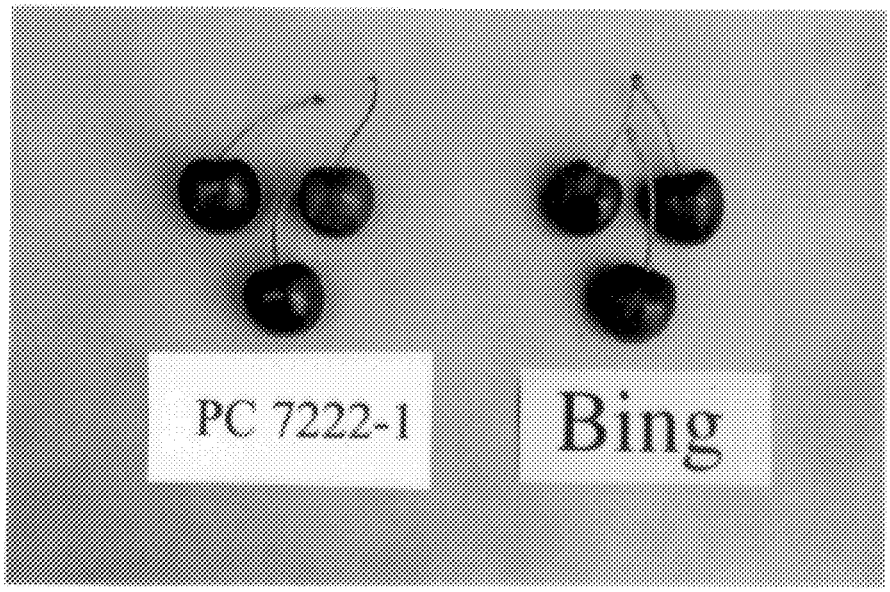
FIG. 2 compares size and shape of mature PC 7222-1 and Bing fruits.
Figure 3:
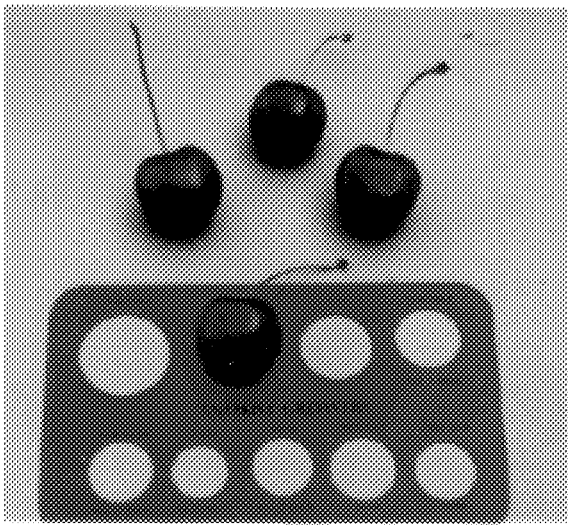
FIG. 3 shows size of mature PC 7222-1 fruits (all cherries pictured are 10 row or larger).
Figure 4:
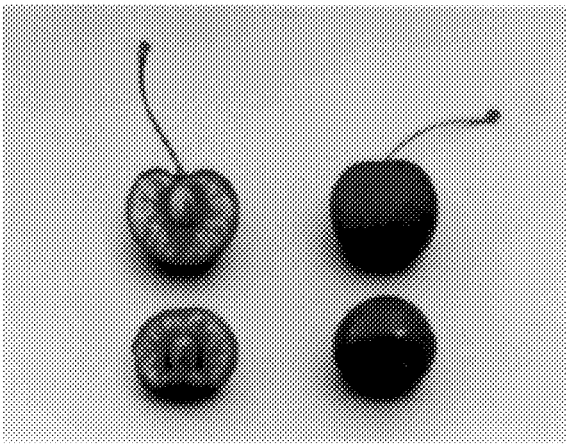
FIG. 4 shows PC 7222-1 fruits with seeds exposed and light-red flesh color.
Figure 5:
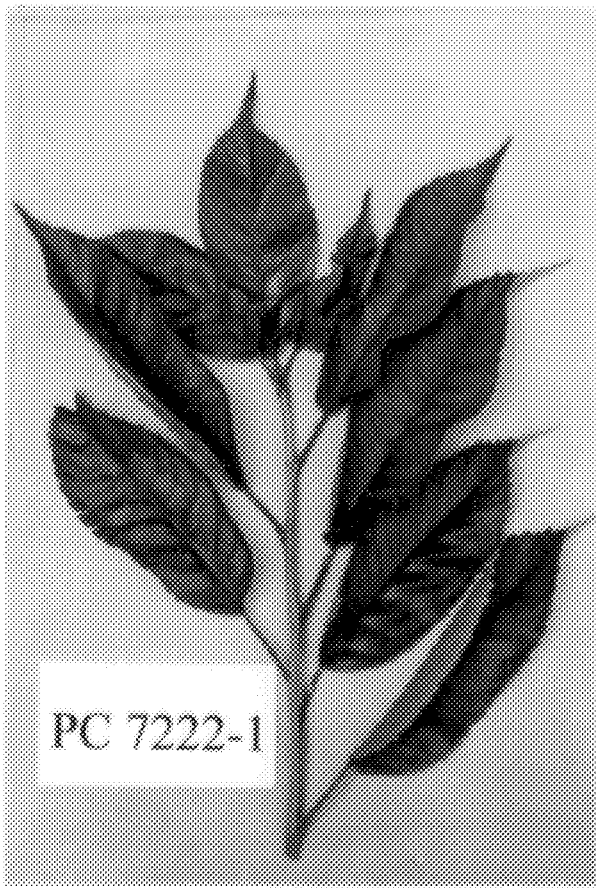
FIG. 5 shows current-season vegetative growth and leaves of the subject variety.

Following is a detailed description of the new variety of cherry tree with color terminology in accordance with the Munsell Color Cascade chart except where general color terms of ordinary dictionary significance are used.

Tree:

*Size.*—Large.

*Vigor.*—Vigorous.

*Branching habit.*—Upright-spreading.

*Density.*—Average for sweet cherry.

*Form.*—Round-headed when mature.

*Hardiness.*—Hardy in area where tested (lower Yakima Valley of Washington).

*Production.*—Very productive.

*Bearing.*—Consistent, regular.

*Trunk.*—Size: Stocky. Bark texture: Typical for sweet cherry. Bark color: Grey-brown (26-13). Lenticels: Numerous, medium 3.2–5.4 mm in diameter, brown.

*Branch.*—Size: Stocky. Texture: Average, typical for sweet cherry. Color: First year wood: greenish-brown (32-10); second year wood: grey-brown (24-12). Lenticels: Numerous, small, 1.5-2.1 mm in diameter, brown.

*Leaves.*—Measurements are from mature leaves attached at midpoint of actively growing upright shoots of current season's growth. Size: Large, 16–17 cm long, 8.5–9 cm wide. Form: Lanceolate with acuminate tip. Color: Upper surface: glossy-green (20-12), lower surface: light-green (17-10). Midvein: Medium, light-red (40-11), 1.5 mm in diameter. Petiole: Medium, 4.5 cm long, thick 2.3 mm, light-green to pink with darker red tinge along petiole groove. Texture: Smooth. Margin: Crenate to finely serrate. Glands: Variable in number but mostly two, compressed, positioned both alternate and irregular, medium, oval to reniform shape, shiny with slightly reddish center when immature, darker red (38-12) when mature, glabrous, positioned on rim of petiole groove 4–7 mm from base of leaf petiole. Stipules: Small, usually two 1.2–1.8 cm in length, light-green (18-8).

*Flower buds.*—Hardiness: Hardy. Size: Medium. Length: Medium. Form: Plump, conic, free.

*Flowers.*—Self-fertile. First bloom: April 5 at Prosser test site (10-year average), early when compared with other varieties. Full bloom: April 12 at Prosser test site. Size: Medium large, 24–30 mm in diameter when fully open. Color: White. Bloom count: Abundant, 5–8 per spur cluster. Petals: Average, 18–20 mm in length and 14–15 mm in width, obovate, cupped slightly inward, white. Nectaries: Light-green when mature (22-7). Anthers: Large, yellow (27-4). Pollen: Abundant, yellow (27-6). Pedicel: Medium length 13–15 mm, light-green (23-6).

*Fruit.*—Maturity: Eating ripe June 11 at Prosser test site (9 year average). Date of first picking: June 11 at Prosser. Date of last picking: June 19 at Prosser. Size: Large, 9.1–9.5 grams, diameter transversely across suture 2.7–2.9 cm, diameter apically 2.4–2.5 cm. Form: Uniform, symmetrical, broadly cordate, rounded apex end. Suture: Very shallow, very slight darker mahogany-colored line extends from base to apex. Stem cavity: Broad, rounded shoulders, shallow. Base: Rounded. Apex: Rounded, pistil point apical and distinctive with very small white dot. Stem: Medium thick, variable 3.5–3.9 cm in length, light-green (21-8). Skin: Thickness: Medium. Texture: Medium. Tenacity: Tenacious to flesh. Tendency to crack: Susceptible to cracking caused by prolonged rains but more tolerant than Bing, none in dry season. Down: Wanting. Color: Mahogany-red (41-15). Flesh: Color: Red (39-9). Surface of pit cavity: Red (38-11). Texture: Very firm, crisp. Fibers: Few, cream color, fine. Ripens: Very evenly. Flavor: Sweet, low acid. Juice: Light-red (39-8). Aroma: Slight. Eating quality: Very good.

*Stone.*—Type: Semi-free. Size: Small, 1.2–1.3 cm long, 0.9 cm wide. Form: Oval with small protruding wing along basal shoulder of ventral suture. Base: Rounded. Helium: Small, oval to slightly oblong. Apex: Rounded. Sides: Equal. Surface: Smooth. Ventral edge: Narrow suture subtended by two low ridges converging basally and apically. Dorsal edge: Narrow, smooth, narrow ridge from base to apex. Color: Tannish-white when dry. Tendency to split: None.

Use: Early season shipping, fresh market.

Keeping quality: Good.

Resistance to insects and diseases: Susceptible to Bacterial Canker (Pseudomonas), no Cherry Crinkle-leaf noted.

Shipping quality: Firm, excellent, at least as good as Bing.

Variance in botanical details: The cherry tree and its fruit herein described will vary due to climatic, soil and growing conditions under which it may be grown. The present description being of the variety as grown in the Lower Yakima Valley of Washington. Comparisons to the Bing variety are referenced to Bing cherry trees growing in the same area under similar circumstances.

I claim:

1. A new and distinct variety of cherry tree obtained as a seedling of Stella (unpatented)×unknown is a self-fertile variety characterized by its early maturing, large, firm fruits that are similar in shape and appearance to the fruits of the Bing variety, but ripen 5–6 days earlier and show no tendency toward Cherry Crinkle-leaf disorder, and by its improved winter hardiness.

* * * * *